United States Patent [19]
Dekeyser et al.

[11] Patent Number: 5,543,404
[45] Date of Patent: Aug. 6, 1996

[54] PESTICIDAL PHENYLHYDRAZINEPHOSPHATES

[75] Inventors: Mark A. Dekeyser, Waterloo, Canada; Paul T. McDonald, Middlebury, Conn.

[73] Assignees: Uniroyal Chemical Company, Inc, Middlebury, Conn.; Uniroyal Chemical Ltd/Ltee, Elmira, Canada

[21] Appl. No.: 498,556

[22] Filed: Jul. 5, 1995

[51] Int. Cl.$^6$ .................. A01N 57/30; C07C 245/02; C07C 243/10

[52] U.S. Cl. .................. 514/118; 514/150; 534/885; 558/154

[58] Field of Search ................ 534/885; 558/154; 514/118,150

[56] References Cited

U.S. PATENT DOCUMENTS

| | | | |
|---|---|---|---|
| 2,906,770 | 9/1959 | Debo | 558/154 X |
| 4,203,932 | 5/1980 | Brown | 558/154 |
| 4,725,302 | 2/1988 | Ehrenfreund | 504/265 |
| 5,367,093 | 11/1994 | Dekeyser | 560/27 |

FOREIGN PATENT DOCUMENTS

| | | |
|---|---|---|
| 0067471 | 12/1982 | European Pat. Off. . |
| 0183650 | 6/1986 | European Pat. Off. . |

OTHER PUBLICATIONS

Chemical Abstracts 108: 163280d (1988).
Chemical Abstracts 105: 152687d (1986).
Rigaudy et al., Chemical Abstracts, 69: 2617e (1968).
Levin et al., Chemical Abstracts, 104: 34140b (1986).

*Primary Examiner*—Fiona T. Powers
*Attorney, Agent, or Firm*—Daniel Reitenbach

[57] ABSTRACT

Compounds having the formula:

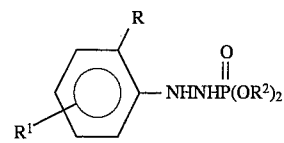

(I)

or

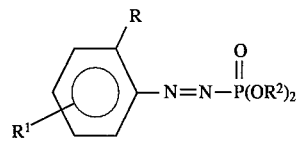
(II)

wherein R is $C_1$–$C_4$ alkoxy, $C_1$–$C_4$ alkyl, hydrogen, halogen, or $C_1$–$C_4$ alkylthio; $R^1$ is phenyl, phenoxy, or benzyl, the phenyl ring of each substituent being optionally substituted with one or more of halogen, nitro, $C_1$–$C_4$ alkyl, $C_1$–$C_4$ alkoxy, $C_1$–$C_4$ haloalkyl or di($C_1$–$C_4$ alkyl)amino; and $R^2$ is branched or straight-chained, $C_1$–$C_6$ alkyl, $C_1$–$C_6$ alkoxy, $C_3$–$C_6$ cycloalkoxy, $C_1$–$C_6$ haloalkyl, alkoxyalkyl, $C_1$–$C_6$ alkenyl, $C_1$–$C_6$ alkylthio, ($C_1$–$C_6$ alkoxy)carbonyl, $C_1$–$C_6$ alkylamino, $C_1$–$C_6$ haloalkoxy, or $C_3$–$C_6$ cycloalkyl. These compounds are effective for controlling mites.

20 Claims, No Drawings

PESTICIDAL PHENYLHYDRAZINEPHOSPHATES

FIELD OF THE INVENTION

This invention is directed to novel phenylhydrazinephosphate derivatives which exhibit activity as miticides.

BACKGROUND OF THE INVENTION

Destruction of crops by mites presents a serious problem to agriculture. A wide variety of field crops are in need of protection from mites including such valuable crops as corn and cotton. In addition, fruits, nuts, ornamentals and seed bed crops such as almonds, apples, pears, citrus fruit and grapes may also require protection from the ravages of such mites. More particularly, the development of pesticides which are effective as both ovicides, larvicides and adulticides are of interest.

Chemical Abstracts 108(19):163280d describes certain alkyl phenylhydrazinecarboxylates and the preparation and acaricidal use thereof. U.S. Pat. No. 4,725,302 describes certain substituted phenylhydrazines and phenyloxadiazolinones and pesticidal uses thereof. European Patent 067 471 describes certain 7-substituted 2,3-dihydrobenzofurans, their preparation, and their use as pesticides or chemical intermediates. DerWent Abstract 88-312695/44 describes certain arylhydrazides of trifluoroacetic acid that have fungicidal, bacteriocidal, acaricidal, and antiseptic activity. U.S. Pat. No. 5,367,093 describes certain insecticidal phenylhydrazine derivatives.

It is the purpose of this to provide novel hydrazine derivatives useful as miticides and nemotacides.

SUMMARY OF THE INVENTION

The present invention relates to a compound having the formula:

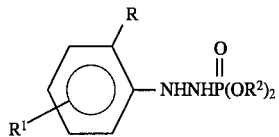

(I)

or

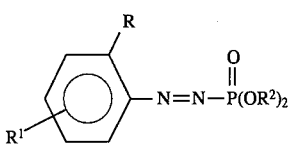

(II)

wherein R is $C_1$–$C_4$ alkoxy, $C_1$–$C_4$ alkyl, hydrogen, halogen, or $C_1$–$C_4$ alkylthio; $R^1$ is phenyl, phenoxy, or benzyl, the phenyl ring of each substituent being optionally substituted with one or more of halogen, nitro, $C_1$–$C_4$ alkyl, $C_1$–$C_4$ alkoxy, $C_1$–$C_4$ haloalkyl or di($C_1$–$C_4$ alkyl)amino; and $R^2$ is branched or straight-chained, $C_1$–$C_6$ alkyl, $C_1$–$C_6$ alkoxy, $C_3$–$C_6$ cycloalkoxy, $C_1$–$C_6$ haloalkyl, alkoxyalkyl, $C_1$–$C_6$ alkenyl, $C_1$–$C_6$ alkylthio, ($C_1$–$C_6$ alkoxy) carbonyl, $C_1$–$C_6$ alkylamino, $C_1$–$C_6$ haloalkoxy, or $C_3$–$C_6$ cycloalkyl. The compounds of formula (I) and (II), and compositions comprising them, have been found to be plant protecting agents for the control of mites.

DETAILED DESCRIPTION OF THE INVENTION

Preferred are those compounds of formula (I) and (II) wherein R is $C_1$–$C_4$ alkoxy or $C_1$–$C_4$ alkyl, $R^1$ is phenyl, and $R^2$ is, branched or straight-chained, $C_1$–$C_4$ alkyl or $C_1$–$C_4$ alkoxy. More preferred is the compound of formula (I) wherein R is $C_1$–$C_4$ alkoxy, $R^1$ is phenyl, and $R^2$ is branched or straight-chained $C_1$–$C_4$ alkyl. Particularly preferred is the compound of formula (I) wherein R is methoxy, $R^1$ is phenyl, and $R^2$ is ethyl or propyl.

The compounds of structure (I) of the instant invention may be prepared by reacting a hydrazine derivative of the formula

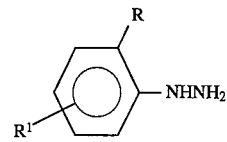

wherein R and $R^1$ are as described above, and a halophosphate of the formula

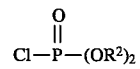

wherein $R^2$ is as described above.

The miticidal compositions of this invention comprise (a) a compound having a structure within that of formula (I) or (II) above and (b) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting miticide composition.

The miticidal compositions may alternatively comprise solid carriers taking the form of dusts, granules, wettable powders, pastes, aerosols, emulsions, emulsifiable concentrates, and water-soluble solids.

For example, the miticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the miticidal compounds may be applied in liquids or sprays when utilized in a liquid carrier, such as in a solution comprising a compatible solvent such as acetone, benzene, toluene or kerosene, or as dispersed in a suitable non-solvent medium, for example, water. Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, and the like.

To combat mites, sprays of the compounds may be applied to the mites directly and/or to plants upon which they feed or nest.

Harmful mites attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as miticides, for foliar application.

The following examples are presented to further illustrate the present invention.

EXAMPLES

Example 1

Preparation of dipropyl 2-(4-methoxy-[1,1'-biphenyl]-3-yl)-hydrazinephosphate (Compound 1)

To 2.5 g of 4-methoxy-[1,1'-biphenyl]-3-amine were added 100 mL of water and 50 mL of concentrated HCL and the stirred mixture was cooled to −5° C. A solution of 1 g of sodium nitrite in 10 mL of water was then added dropwise, maintaining a temperature of −5° C. After this addition, the mixture was stirred at −5° C. for 1 hour. A solution of 10 g of stannous chloride in 20 mL of concentrated HCL was added quickly to the reaction mixture which was then stirred for 1 hour, then neutralized with sodium hydroxide and extracted with dichloromethane. Evaporation of the dichloromethane gave 1.5 g of an oil which was then dissolved in 100 mL of toluene. To this solution was added 2 g of dipropyl chlorophosphate and the resulting mixture was refluxed for 2 hours. Upon evaporation of the toluene, 3 g of a waxy solid remained.

Compound 2 shown in Table 1 below was prepared using an analogous procedure. Compounds 1 and 2 are characterized by their proton NMR characteristics.

TABLE I 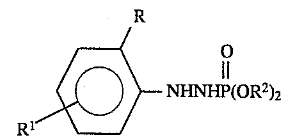 (I)

| Compound No. | R | $R^1$ | $R^2$ | NMR Data ($CDCL_3$ PPM) |
|---|---|---|---|---|
| 1 | $OCH_3$ | $C_6H_5$ | $C_3H_7$ | t(6)1.0; m(4)1.9; s(3)3.9; m(4)4.1; m(8)7.0–7.6 |
| 2 | $OCH_3$ | $C_6H_5$ | $C_2H_5$ | t(6)1.0; s(3)3.9; q(6)4.1; m(8)7.0–7.6 |

Example 2

Preparation of Formulations

The remaining examples relate to the pesticidal use of the compounds of this invention. In all these examples a stock solution for each of the compounds was prepared at 3000 ppm by dissolving 0.3 gram of each compound to be tested in 10 ml of acetone and adding 90 ml of distilled water plus four drops of ethoxylated sorbitan monolaurate, or a simliar suitable wetting agent, to provide a stock solution for each tested compound. For each example that follows, this stock solution was used ahd the specificied dilutions made. All the tests discussed below, which involved treatment with compounds of this invention at concentrations of 500 and 40 ppm, were always repeated with controls, in which the active compound was not provided, to permit a comparison upon which the percent control was calculated.

Example 3

Mite Adulticide and Mite Ovicide/Larvicide Tests

One day before treatment, a "FIG. 8" configuartion of tree tanglefoot was applied to each of two cowpea primary leaves, one from each of two plants in a pot. In each figure, the circle nearer the stem was designated for the mite ovicide/larvicide test and the circle further from the stem was designated for the mite adulticide test.

Groups of adult mites (*Tetranychus urticae* Koch) were transferred into ovicide circles one day before treatment and the females were allowed to deposit eggs until one hour before treatment when all mites were removed. Plants were sprayed to run off with a 1000 ppm solution diluted from the 3000 ppm stock solution.

One day following treatment, groups of approximately 25 adult mites were transferred into the adulticide rings. Five days later these rings were examined for live mites remaining on the leaves. The percent control was estimated based on the number of mites surviving on the plants.

Nine days following treatment the ovicide/larvicide rings were examined for hatched eggs and living immature mites. The percent control was estimated based on the number of eggs hatching and immature mites surviving on the plants. When the treatment effect was to eggs, control was designated as ovicidal (O); when the treatment effect was to immatures, control was designated as larvicidal (L).

Results of the mite adulticide (MI) and ovicide/larvicide (MIOLV) tests are presented in Table 2 below.

TABLE 2

| Compound No. | Percent Control | |
| --- | --- | --- |
|  | MI | MIOVL |
| 1 | 100 | 100(O) |
| 2 | 100 | 70(L) |

What is claimed is:

1. A compound of the formula:

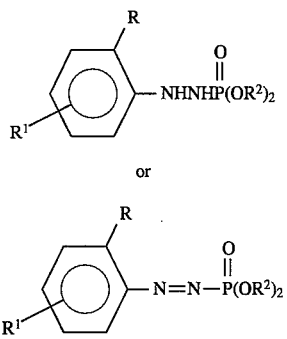

wherein R is $C_1-C_4$ alkoxy, $C_1-C_4$ alkyl, hydrogen, halogen, or $C_1-C_4$ alkylthio; $R^1$ is phenyl, phenoxy, or benzyl, the phenyl ring of each substituent being optionally substituted with one or more of halogen, nitro, $C_1-C_4$ alkyl, $C_1-C_4$ alkoxy, $C_1-C_4$ haloalkyl or di($C_1-C_4$ alkyl)amino; and $R^2$ is branched or straight-chained, $C_1-C_6$ alkyl, $C_1-C_6$ alkoxy, $C_3-C_6$ cycloalkoxy, $C_1-C_6$ haloalkyl, alkoxyalkyl, $C_1-C_6$ alkenyl, $C_1-C_6$ alkylthio, ($C_1-C_6$ alkoxy) carbonyl, $C_1-C_6$ alkylamino, $C_1-C_6$ haloalkoxy, or $C_3-C_6$ cycloalkyl.

2. A compound as recited in claim 1 wherein R is $C_1-C_4$ alkoxy or $C_1-C_4$ alkyl.

3. A compound as recited in claim 2 wherein R is $C_1-C_4$ alkoxy.

4. A compound as recited in claim 3 wherein R is methoxy.

5. A compound as recited in claim 1 wherein $R^1$ is phenyl.

6. A compound as recited in claim 1 wherein $R^2$ is, branched or straight-chained, $C_1-C_4$ alkyl or $C_1-C_4$ alkoxy.

7. A compound as recited in claim 6 wherein $R^2$ is branched or straight-chained $C_1-C_4$ alkyl.

8. A compound as recited in claim 7 wherein $R^2$ is ethyl or propyl.

9. A compound as recited in claim 1 of the formula

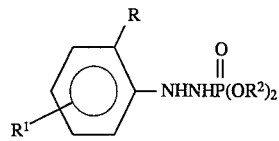

wherein R, $R^1$ and $R^2$ are as defined in claim 1.

10. A compound as recited in claim 9 wherein R is $C_1-C_4$ alkoxy or $C_1-C_4$ alkyl, $R^1$ is phenyl, and $R^2$ is, branched or straight-chained, $C_1-C_4$ alkyl or $C_1-C_4$ alkoxy.

11. A compound as recited in claim 10 wherein R is $C_1-C_4$ alkoxy, $R^1$ is phenyl, and $R^2$ is branched or straight-chained $C_1-C_4$ alkyl.

12. A compound as recited in claim 11 wherein R is methoxy, $R^1$ is phenyl, and $R^2$ is ethyl or propyl.

13. A compound as recited in claim 1 of the formula

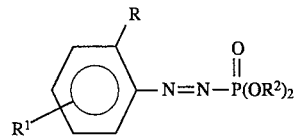

wherein R, $R^m$ and $R^2$ are as defined in claim 1.

14. A miticidal composition comprising a miticidally effective amount of a compound as recited in claim 1 and an acceptable carrier.

15. A miticidal composition comprising a miticidally effective amount of a compound as recited in claim 9 and an acceptable carrier.

16. A miticidal composition comprising a miticidally effective amount of a compound as recited in claim 10 and an acceptable carrier.

17. A method for controlling undesirable mites which comprises applying to a locus to be protected a miticidally effective amount of a compound as recited in claim 13.

18. A method for controlling undesirable mites which comprises applying to a locus to be protected a miticidally effective amount of a compound as recited in claim 1.

19. A method for controlling undesirable mites which comprises applying to a locus to be protected a miticidally effective amount of a compound as recited in claim 9.

20. A method for controlling undesirable mites which comprises applying to a locus to be protected a miticidally effective amount of a compound as recited in claim 13.

* * * * *